United States Patent
Hirama

(10) Patent No.: US 10,882,923 B2
(45) Date of Patent: *Jan. 5, 2021

(54) LOW-SUBSTITUTED HYDROXYPROPYL CELLULOSE, PRODUCTION METHOD THEREOF, AND SOLID PREPARATION

(71) Applicant: SHIN-ETSU CHEMICAL CO., LTD., Tokyo (JP)

(72) Inventor: Yasuyuki Hirama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 515 days.

This patent is subject to a terminal disclaimer.

(21) Appl. No.: 15/722,588

(22) Filed: Oct. 2, 2017

(65) Prior Publication Data

US 2018/0100029 A1    Apr. 12, 2018

(30) Foreign Application Priority Data

Oct. 7, 2016 (JP) .................................. 2016-199098

(51) Int. Cl.
| | |
|---|---|
| C08B 11/08 | (2006.01) |
| A61K 31/167 | (2006.01) |
| A61K 9/20 | (2006.01) |
| C08B 11/193 | (2006.01) |
| C08B 11/20 | (2006.01) |
| C08L 1/32 | (2006.01) |
| C09D 101/30 | (2006.01) |
| A61K 47/38 | (2006.01) |
| A61K 9/14 | (2006.01) |

(52) U.S. Cl.
CPC ............ *C08B 11/08* (2013.01); *A61K 9/2054* (2013.01); *A61K 9/2095* (2013.01); *A61K 31/167* (2013.01); *C08B 11/193* (2013.01); *C08B 11/20* (2013.01); *A61K 9/146* (2013.01); *A61K 47/38* (2013.01); *C08L 1/32* (2013.01); *C09D 101/30* (2013.01)

(58) Field of Classification Search
CPC .... A61K 9/2054; A61K 9/2095; A61K 9/146; A61K 31/167; A61K 47/38; C08B 3/08; C08B 3/14; C08B 11/08; C08B 11/20; C08B 11/193; A61J 3/10; C08L 1/284; C08L 1/32; C09D 101/30; G01N 23/20
See application file for complete search history.

(56) References Cited

U.S. PATENT DOCUMENTS

| 4,091,205 A | 5/1978 | Onda et al. |
| 10,513,565 B2 | 12/2019 | Hirama et al. |
| 2003/0166918 A1 | 9/2003 | Obara |
| 2008/0038339 A1 | 2/2008 | Hoshino et al. |
| 2008/0039621 A1 | 2/2008 | Maruyama et al. |
| 2011/0230656 A1 | 9/2011 | Maruyama et al. |
| 2015/0299338 A1 | 10/2015 | Yoshida |

FOREIGN PATENT DOCUMENTS

| EP | 1342733 A1 | 9/2003 |
| EP | 2366720 A1 | 9/2011 |
| EP | 2659880 A1 | 11/2013 |
| EP | 2937363 A1 | 10/2015 |
| GB | 482885 A | 4/1938 |
| JP | S51-063927 A | 6/1976 |
| JP | 2008-133432 A | 6/2008 |
| JP | 2011-195665 A | 10/2011 |
| JP | 2014-510137 A | 4/2014 |
| JP | 2018-062653 A | 4/2018 |
| WO | 2012/138529 A1 | 10/2012 |

OTHER PUBLICATIONS

U.S. Appl. No. 15/722,594, filed Oct. 2, 2017 in the name of Hirama et al.
Mar. 21, 2018 Extended European Search Report issued in Patent Application No. 17195313.6.
Mar. 21, 2018 Extended European Search Report issued in Patent Application No. 17195312.8.
Brännvall, Elisabet et al., "Pulp Characterisation.", Pulping Chemistry and Techno, De Gruyter, pp. 429-459.
Jan. 10, 2019 U.S. Office Action issued in U.S. Appl. No. 15/722,594.
Nov. 16, 2020 Office Action issued in Japanese Patent Application No. 2017-194968.
"Dictionary of Cellulose;" First Edition; Asakura Publishng Co., Ltd.; pp. 410-412; Nov. 10, 2000.

*Primary Examiner* — Holly C Rickman
*Assistant Examiner* — Lisa Chau
(74) *Attorney, Agent, or Firm* — Oliff PLC

(57) ABSTRACT

There are provided low-substituted hydroxypropyl cellulose (L-HPC) having good compressibility and capping-prevention performance, and others. Specifically, provided are L-HPC having a hydroxypropoxy content of 5 to 16% by weight, a volume fraction of long fibrous particles of 20 to 40% and a volume fraction of short fibrous particles of 26 to 60% with the proviso that the latter is greater than the former; and a solid preparation containing the L-HPC. Also provided is a method for producing the L-HPC including the steps of: bringing powdery pulp having a length-weighted mean width of 10 to 25 μm into contact with an alkali metal hydroxide solution, reacting the alkali cellulose with propylene oxide, and neutralizing the alkali metal hydroxide present in the reaction product with an acid to precipitate crude low-substituted hydroxypropyl cellulose in the absence of a step of dissolving a portion or all of the reaction product.

13 Claims, 1 Drawing Sheet

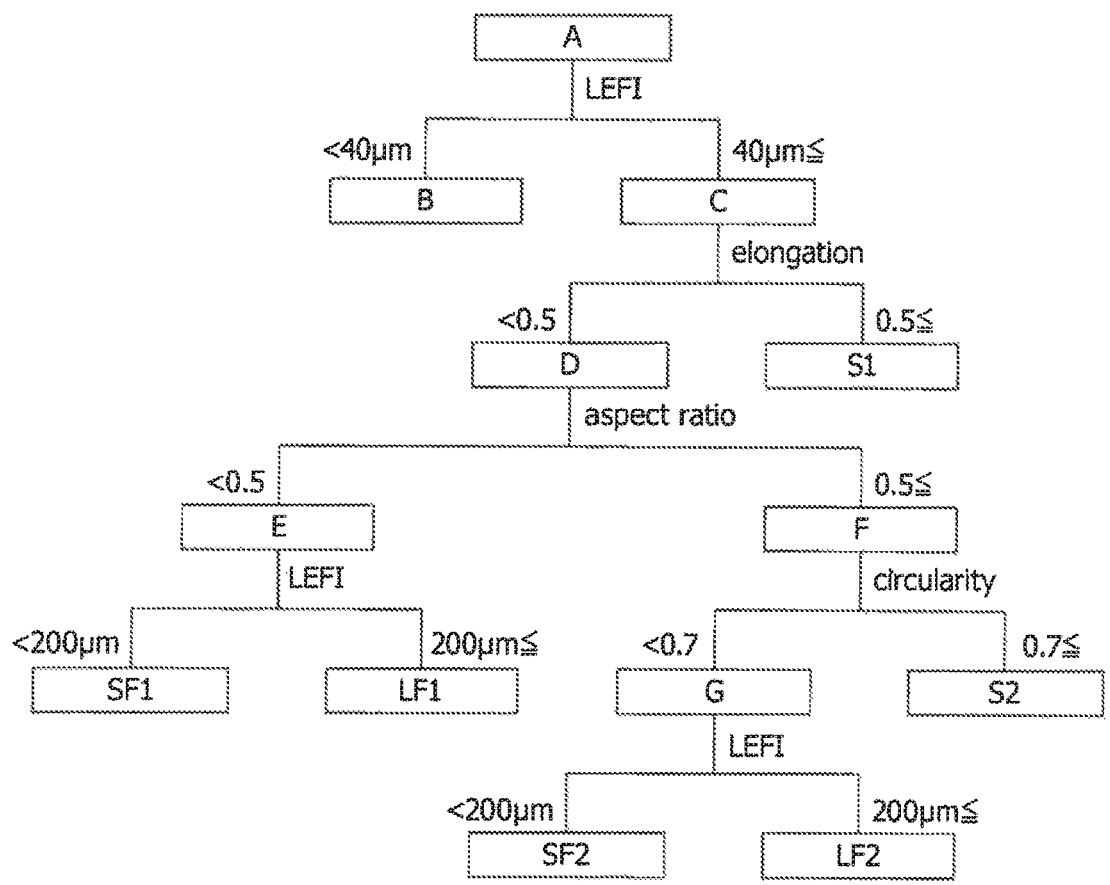

LOW-SUBSTITUTED HYDROXYPROPYL CELLULOSE, PRODUCTION METHOD THEREOF, AND SOLID PREPARATION

BACKGROUND OF THE INVENTION

1. Field of the Invention

The invention relates to low-substituted hydroxypropyl cellulose to be added as a disintegrant or a binder to a solid preparation in the fields of pharmaceuticals or food, the low-substituted hydroxypropyl cellulose having good compressibility and capping-prevention performance.

2. Related Art

A solid preparation as a pharmaceutical product, healthy food or the like disintegrates since a disintegrant contained therein absorbs water and swells therein. Examples of the disintegrant include low-substituted hydroxypropyl cellulose, carboxymethyl cellulose and a calcium salt thereof, and starch and a derivative thereof.

Particularly in the field of pharmaceuticals, the number of newly developed drugs which lack stability is increasing and an additive therefor has been limited from the standpoint of their mutual action. Under the circumstances, the low-substituted hydroxypropyl cellulose has been used widely as a nonionic disintegrant or binder and can be regarded as a preferable additive.

A tablet, which is one of the dosage forms of the solid preparation as a pharmaceutical product or food, is a solid preparation obtained by compressing powder into a predetermined shape. The tablet has advantages such as handling ease. Particularly in the fields of pharmaceuticals, a production amount of the tablet is about 50% of the total production amount of pharmaceuticals. Thus, the tablet is the most popular dosage form.

The tablet can be produced by, for example, a dry direct tableting method, a dry granulation tableting method, an extrusion granulation tableting method, or a wet granulation tableting method. The dry direct tableting method is a method of directly tableting a mixture of a drug, an excipient and the like into a tablet. The dry direct tableting method is more advantageous than the wet granulation tableting method because the dry direct tableting method can omit granulation, drying and sizing steps, thereby making the process simple and the production cost reduced greatly. On the other hand, the dry direct tableting method is more likely to cause problems such as uneven drug contents, variation in tablet weight, and a tableting trouble, compared with the wet granulation tableting method. The tableting trouble mean a trouble happening during tableting and typical examples of the tableting trouble include sticking, binding, and capping. In particular, the capping is a tableting trouble in which a portion of a tablet separates to form a cap. The capping results in not only an unusual appearance but also reduction of the drug content so that the capping should be prevented.

There is known a method of controlling the amount of particles in fibrous form by dispersing the etherification reaction product in water containing an acid in such an amount as to be from 5 to 80% of the amount required for neutralizing the total amount of alkali to dissolve a portion of low-substituted hydroxypropyl cellulose therein (JP 51-063927A). The low-substituted hydroxypropyl cellulose produced by the above method has good compressibility due to entanglement among fibrous particles so that the capping can be prevented in the dry direct tableting method or wet granulation tableting method.

There is also known a method of decreasing the amount of particles in fibrous form by neutralizing all the alkali present in the etherification reaction product without dissolving a portion of the low-substituted hydroxypropyl cellulose, and subjecting to compaction-grinding (JP 2008-133432A). The low-substituted hydroxypropyl cellulose obtained by this method has good flowability and has compressibility better than that of the low-substituted hydroxypropyl cellulose of JP 51-063927A in spite of the absence of the particles in fibrous form.

SUMMARY OF THE INVENTION

However, when the low-substituted hydroxypropyl cellulose described in JP 51-063927A or JP 2008-133432A is used for the dry direct tableting or the like, the capping may occur due to insufficient compressibility. Thus, there is a demand for further improvement in compressibility.

The invention has been made to overcome the drawback of the above-described prior art. An object of the invention is to provide low-substituted hydroxypropyl cellulose having good compressibility and capping-prevention performance.

As a result of an extensive investigation with a view to achieving the object, the inventors have found that low-substituted hydroxypropyl cellulose having long and short fibrous particles at controlled proportions shows good compressibility and capping-prevention performance, and have completed the invention.

In one aspect of the invention, there is provided low-substituted hydroxypropyl cellulose having a hydroxypropoxy content of from 5 to 16% by weight, and having, on a basis of a dynamic image analysis to divide all particles into fine particles, spherical particles, and fibrous particles consisting of long and short fibrous particles, a volume fraction of the long fibrous particles relative to all of the particles of from 20 to 40% and a volume fraction of the short fibrous particles relative to all of the particles of from 26 to 60% with the proviso that the volume fraction of the short fibrous particles is greater than the volume fraction of the long fibrous particles, wherein the fine particles have a length of fiber of less than 40 μm, the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimal Feret diameter to a maximal Feret diameter, of 0.5 or more, and a circularity, which is a ratio of a perimeter ($P_{EQPC}$) of a circle that has the same area as a projection area to a perimeter ($P_{real}$) of a real particle, of 0.7 or more, the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7, and the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

In another aspect of the invention, there is provided a solid preparation comprising the low-substituted hydroxypropyl cellulose.

In a further aspect of the invention, there is provided a method for producing the low-substituted hydroxypropyl cellulose, comprising the steps of: bringing powdery pulp having a length-weighted mean width of from 10 to 25 μm into contact with an alkali metal hydroxide solution to obtain alkali cellulose; reacting the alkali cellulose with propylene oxide to obtain a reaction product; neutralizing the alkali metal hydroxide present in the reaction product with an acid to precipitate crude low-substituted hydroxypropyl cellulose, in the absence of a step of dissolving a portion or all of the reaction product; washing the crude low-substituted hydroxypropyl cellulose to obtain washed low-substituted hydroxypropyl cellulose; drying the washed low-substituted hydroxypropyl cellulose to obtain dried low-substituted hydroxypropyl cellulose; and pulverizing the dried low-substituted hydroxypropyl cellulose.

According to the invention, since the low-substituted hydroxypropyl cellulose has good compressibility and capping-prevention performance, a high-quality solid preparation can be produced. For example, a high-quality tablet causing less capping during tableting, coating, filling, transporting or the like can be produced. In addition, high-quality granules or the like causing less cracks during filling, transporting or the like can be produced.

BRIEF DESCRIPTION OF THE DRAWINGS

FIG. 1 is a flowchart of dividing the "all particles" of low-substituted hydroxypropyl cellulose into four types of particles, "fine particles", "long fibrous particles (LF1 and LF2)", "short fibrous particles (SF1 and SF2)", and "spherical particles (S1 and S2)".

DETAILED DESCRIPTION OF THE PREFERRED EMBODIMENTS

In the specification, low-substituted hydroxypropyl cellulose is divided into four types of particles, "long fibrous particles", "short fibrous particles", "spherical particles", and "fine particles". FIG. 1 is a flowchart that summarizes the division of "all particles" of a hydroxyalkyl alkyl cellulose into four types of particles, "fine particles", "long fibrous particles (LF1 and LF2)", "short fibrous particles (SF1 and SF2)", and "spherical particles (S1 and S2)".

Each volume fraction of the respective types of particles of low-substituted hydroxypropyl cellulose can be determined by measuring shape parameters including a length of fiber (LEFI), a diameter of fiber (DIFI), an elongation, an aspect ratio, and a circularity, by the dynamic image analysis. The dynamic image analysis is a method in which images of particles dispersed in a fluid such as a gas and a solvent are continuously recorded and are binarized and analyzed to obtain a particle diameter or a particle shape. The analysis can be performed by using, for example, a dynamic image analysis type particle diameter distribution analyzer, QICPIC/R16 manufactured by Sympatec GmbH).

All particles A are divided into particles C having a length of fiber (LEFI) of 40 μm or more and fine particles B having a length of fiber of less than 40 μm. The LEFI is defined as the length of the longest direct path that connects the ends of the particle within the contour of the particle. A QICPIC/R16 equipped with an M7 lens has a detection limit of 4.7 μm and thus fails to detect a particle having an LEFI of less than 4.7 μm. However, the volume of particles having an LEFI of less than 4.7 μm is extremely small relative to that of all particles of the low-substituted hydroxypropyl cellulose so that it is negligible for the purpose of the invention.

The particles C having an LEFI of 40 μm or more are divided into first spherical particles (S1) having an elongation of 0.5 or more and particles D having an elongation of less than 0.5, wherein the elongation is a ratio of a diameter of fiber (DIFI) to LEFI (DIFI/LEFI) of the particle. The DIFI is defined as the minor diameter of a particle, and is calculated by dividing the projection area of the particle by the sum of all lengths of the fiber branches of the particle.

The particles D having an LEFI of 40 μm or more and an elongation of less than 0.5 are divided into particles E having an aspect ratio of less than 0.5 and particles F having an aspect ratio of 0.5 or more, wherein the aspect ratio is a ratio ($F_{min}/F_{max}$) of minimal Feret diameter ($F_{min}$) to maximal Feret diameter ($F_{max}$). Each particle has an aspect ratio of more than 0 and not more than 1. The Feret diameter is the distance between two parallel tangent lines that put the particle therebetween. The maximal Feret diameter ($F_{max}$) is the largest distance between pairs of tangent lines to the particle in consideration of all possible orientations by changing the directions from 00 to 180°, and the minimal Feret diameter ($F_{min}$) is a minimal distance between pairs of tangent lines to the particle in consideration of all possible orientations by changing the directions from 00 to 180°.

The fibrous particles E having an LEFI of 40 μm or more, an elongation of less than 0.5, and an aspect ratio of less than 0.5 are divided into first long fibrous particles (LF1) having an LEFI of 200 μm or more and first short fibrous particles (SF1) having an LEFI of less than 200 μm.

The particles F having an LEFI of 40 μm or more, an elongation of less than 0.5, and an aspect ratio of 0.5 or more are divided into second spherical particles (S2) having a circularity of 0.7 or more and fibrous particles G having a circularity of less than 0.7. The circularity is a ratio of the perimeter ($P_{EQPC}$) of a circle that has the same area as the projection area ($A_p$) of the particle to the perimeter ($P_{real}$) of the real particle, and is defined by the following equation. Each particle has a circularity of more than 0 and not more than 1. A particle having a smaller circularity has a more irregular shape. The EQPC is the diameter of a circle of an equal projection area, and is defined as the diameter of a circle that has the same area as the projection area of the particle, and is also called Heywood diameter.

$$\text{Circularity} = P_{EQPC}/P_{real} = 2\sqrt{\pi \cdot A_p}/P_{real}$$

The fibrous particles G having an LEFI of 40 μm or more, an elongation of less than 0.5, an aspect ratio of 0.5 or more, and a circularity of less than 0.7 are divided into second long fibrous particles (LF2) having an LEFI of 200 pun or more and second short fibrous particles (SF2) having an LEFI of less than 200 μm.

The volume ($V_m$) of the fine particles of low-substituted hydroxypropyl cellulose can be calculated by the following equation where each fine particle is assumed to be a sphere having a diameter of EQPC.

$$V_m = (\pi/6) = (EQPC)^3 \times N_m,$$

wherein $N_m$ is the number of fine particles in a sample, and EQPC is a median EQPC corresponding to the 50% cumulative value on a number-based cumulative particle diameter distribution curve of the fine particles.

In the specification, particles having an LEFI of 40 μm or more, which are particles other than the fine particles having an LEFI of less than 40 μm among the all particles, are divided, on the basis of such above shape parameters of particles as LEFI, an elongation, an aspect ratio, and a circularity, into "long fibrous particles", "short fibrous particles", and "spherical particles", which are distinguished from each other.

<Long Fibrous Particles>

Particles satisfying the following definition of LF1 or LF2 are combined into "long fibrous particles".

LF1: particles having an elongation of less than 0.5, an aspect ratio of less than 0.5, and an LEFI (length of fiber) of 200 μm or more, and LF2: particles having an elongation of less than 0.5, an aspect ratio of 0.5 or more, a circularity of less than 0.7, and an LEFI (length of fiber) of 200 μm or more.

The volume ($V_{LF}$) of the long fibrous particles of low-substituted hydroxypropyl cellulose can be calculated by the following equation wherein each long fibrous particle is assumed to be a cylindrical column having a DIFI as a bottom diameter and an LEFI as a height.

$$V_{LF}=(\pi/4)\times(DIFI)^2\times(LEFI)\times N_{LF},$$

wherein $N_{LF}$ is the number of long fibrous particles in the sample, DIFI is a median DIFI corresponding to the 50% cumulative value on a number-based cumulative particle diameter distribution curve of the long fibrous particles, and LEFI is a median LEFI corresponding to the 50% cumulative value on a number-based cumulative particle diameter distribution curve of the long fibrous particles.

The volume of particles satisfying the definition LF and the volume of particles satisfying the definition LF2 are calculated in accordance with the above equation, respectively, and a sum of the volumes means the volume of the long fibrous particles of a hydroxyalkyl alkyl cellulose.

<Short Fibrous Particles>

Particles satisfying the following definition of SF1 or SF2 are combined into "short fibrous particles".

SF1: particles having an elongation of less than 0.5, an aspect ratio of less than 0.5, and an LEFI (length of fiber) of not less than 40 μm and less than 200 μm, and SF2: particles having an elongation of less than 0.5, an aspect ratio of 0.5 or more, a circularity of less than 0.7, and an LEFI (length of fiber) of not less than 40 μm and less than 200 μm.

The volume ($V_{SF}$) of the short fibrous particles of low-substituted hydroxypropyl cellulose can be calculated by the following equation where each short fibrous particle is assumed to be a cylindrical column having a bottom diameter of DIFI and a height of LEFI, in the same manner as for the above long fibrous particles.

$$V_{SF}=(\pi/4)\times(DIFI)^2\times(LEFI)\times N_{SF},$$

wherein $N_{SF}$ is the number of short fibrous particles in the sample, DIFI is a median DIFI corresponding to the 50% cumulative value on a number-based cumulative particle diameter distribution curve of the short fibrous particles, and LEFI is a median LEFI corresponding to the 50% cumulative value on a number-based cumulative particle diameter distribution curve of the short fibrous particles.

The volume of particles satisfying the definition of SF1 and the volume of particles satisfying the definition of SF2 are calculated in accordance with the above equation, respectively, and a sum of the volumes means the volume of the short fibrous particles of low-substituted hydroxypropyl cellulose.

<Spherical Particles>

Particles satisfying the definition of S1 or S2 are combined into "spherical particles".

S1: particles having an LEFI (length of fiber) of 40 μm or more, and an elongation of 0.5 or more, and S2: particles having an LEFI (length of fiber) of 40 μm or more, an elongation of less than 0.5, an aspect ratio of 0.5 or more, and a circularity of 0.7 or more.

The volume ($V_S$) of the spherical particles of low-substituted hydroxypropyl cellulose can be calculated by the following equation where each spherical particle is assume to be a sphere having a diameter of EQPC.

$$V_S=(\pi/6)\times(EQPC)^3\times N_S,$$

wherein $N_S$ is the number of spherical particles in the sample, and EQPC is a median EQPC corresponding to the 50% cumulative value on a number-based cumulative particle diameter distribution curve of the spherical particles.

The volume of particles satisfying the definition S1 and the volume of particles satisfying the definition S2 are calculated in accordance with the above equation, respectively, and a sum of the volumes means the volume of the spherical particles of low-substituted hydroxypropyl cellulose.

The volume fraction of each type of particles of low-substituted hydroxypropyl cellulose can be calculated from the following corresponding equation on a basis of the above-defined volumes, $V_m$, $V_{LF}$, $V_{SF}$, and $V_S$.

Volume fraction of fine particles=$\{V_m/(V_m+V_{LF}+V_{SF}+V_S)\}\times 100$

Volume fraction of long fibrous particles=$\{V_{LF}/(V_m+V_{LF}+V_{SF}+V_S)\}\times 100$ Volume fraction of short fibrous particles=$\{V_{SF}/(V_m+V_{LF}+V_{SF}+V_S)\}\times 100$ Volume fraction of spherical particles=$\{V_S/(V_m+V_{LF}+V_{SF}+V_S)\}\times 100$ The low-substituted hydroxypropyl cellulose has a volume fraction of long fibrous particles of from 20 to 40%, preferably from 22 to 35%, more preferably from 24 to 30% from the standpoint of good flowability, high compressibility, and capping-prevention performance.

The low-substituted hydroxypropyl cellulose has a volume fraction of short fibrous particles of from 26 to 60%, preferably from 35 to 55%, more preferably from to 50% from the standpoint of good flowability, high compressibility, and capping-prevention performance.

The low-substituted hydroxypropyl cellulose has a ratio of the volume fraction of short fibrous particles to the volume fraction of long fibrous particles (short fibrous particles/long fibrous particles) of preferably from 1.35 to 2.50, more preferably from 1.40 to 2.40, still more preferably from 1.50 to 2.30, from the standpoint of flowability improvement.

The low-substituted hydroxypropyl cellulose has a volume fraction of fibrous particles, in other words, a total volume fraction of long fibrous particles and short fibrous particles of preferably from 60 to 85%, more preferably from 65 to 80%, still more preferably from 70 to 75%, from the standpoint of good flowability, high compressibility and capping-prevention performance.

The low-substituted hydroxypropyl cellulose has a volume fraction of spherical particles of preferably from 15 to 35%, more preferably from 18 to 30%, still preferably from 20 to 28%, from the standpoint of good flowability and capping-prevention performance.

The low-substituted hydroxypropyl cellulose has a volume fraction of fine particles of preferably less than 10.0%, more preferably less than 8.0%, still more preferably less than 5.0%, from the standpoint of good flowability.

The low-substituted hydroxypropyl cellulose has a hydroxypropoxy content of from 5 to 16% by weight, preferably from 6 to 15% by weight, more preferably from 7 to 14% by weight. Low-substituted hydroxypropyl cellulose having a hydroxypropoxy content of less than 5% by weight has low swelling by water absorption. Low-substituted hydroxypropyl cellulose having a hydroxypropoxy content of more than 16% by weight has an increased water solubility so that a solid preparation comprising it has insufficient disintegrability. The hydroxypropoxy content can be determined by the assay described in the "low-substituted hydroxypropyl cellulose" of the Japanese Pharmacopoeia Seventeenth Edition.

The low-substituted hydroxypropyl cellulose has a volume-based average particle diameter, determined by a dry laser diffractometry, of preferably from 10 to 120 μm, more preferably from 30 to 100 μm, still more preferably from 40 to 90 μm, particularly preferably from 50 to 70 μm, from the standpoint of disintegrability and compressibility. The volume-based average particle diameter means a diameter corresponding to the 50% cumulative value of a volume-based cumulative particle diameter distribution curve, and it may be measured using, for example, a laser diffraction particle diameter distribution analyzer "Mastersizer 3000" (produced by Malvern Instruments Ltd).

The low-substituted hydroxypropyl cellulose may be used as a binder or disintegrant of a solid preparation such as a tablet, a granule, a fine granule or a capsule. The low-substituted hydroxypropyl cellulose is particularly suited as a tablet, which is easy to handle and most popularly used. The tablet may be obtained by any one of the dry direct tableting method, the wet mixing granulation tableting method, the fluidized-bed granulation tableting method, and the dry granulation tableting method. The dry direct tableting method is particularly suited because its production process is simple and contains production steps more simplified than those of the wet mixing granulation tableting method and others, thereby greatly reducing a production cost.

The term "granule" or "fine granule" means a product obtained by granulating a mixture containing at least the low-substituted hydroxypropyl cellulose and a drug. The capsule may be produced by encapsulating the granules or fine granules.

The low-substituted hydroxypropyl cellulose content in the solid preparation is preferably from 2 to 50% by weight, more preferably from 5 to 30% by weight, still more preferably from 5 to 20% by weight, from the standpoint of compressibility, disintegrability and storage stability.

A method for producing a tablet comprising the low-substituted hydroxypropyl cellulose by the dry direct tableting method will next be described. In the dry direct tableting method, a tablet may be produced by a method comprising a step of compressing a mixture of at least the low-substituted hydroxypropyl cellulose, a drug and a lubricant with a tableting machine at a predetermined pressure. The drug may be in any one of the following forms: fine powder, crude particles, and a granulated product. The lubricant is used in an amount of preferably from 0.05 to 2.0 parts by weight relative to 100 parts by weight of the mixture containing at least the low-substituted hydroxypropyl cellulose and the drug (excluding the lubricant).

A tablet may be produced by using a tableting machine such as a rotary tableting machine or a single-punch tableting machine. The size of the tablet may be selected freely. A tablet diameter is preferably from 6 to 12 mm from the standpoint of handling ease and ingestability, and a tablet weight (i.e. weight per tablet) is preferably from 70 to 700 mg The tableting pressure during tableting is preferably from 50 to 300 MPa from the standpoint of tablet hardness and reduction of tableting troubles.

The capping incidence of tablets is preferably 0% from the standpoint of the quality of the tablets. The capping incidence can be determined by the method comprising the steps of: turning a drum having 50 tablets therein 100 times for 4 minutes at 25 rpm, and counting the number of tablets which have caused capping by using a tablet friability tester described in "Tablet Friability Test" of the Japanese Pharmacopoeia Seventeenth Edition. For example, it can be measured using a friability tester TA (product of ERWEKA GmbH).

The low-substituted hydroxypropyl cellulose has compressibility of preferably 250N or more, more preferably 300N or more, still more preferably 350N or more from the standpoint of tablet hardness or reduction of capping incidence.

The compatibility of the low-substituted hydroxypropyl cellulose means the hardness of a tablet obtained by compressing 450 mg of the low-substituted hydroxypropyl cellulose having such a controlled humidity as to have a loss on drying (i.e. water content) of from 2.8 to 3.8% by weight, with a single-punch tableting machine using a round flat type punch having a diameter of 12 mm at a tableting pressure of 10.0 kN (about 88.5 MPa).

The loss on drying (i.e. water content) can be determined by the method described in "Loss on Drying test" in "General Tests" of the Japanese Pharmacopoeia Seventeenth Edition.

The hardness of the tablet can be measured from the maximum strength at break at which the tablet is broken by a load applied at a predetermined rate in the diameter direction of the tablet. For example, it can be measured using a tablet hardness tester "TBH-125" (product of ERWEKA GmbH).

The low-substituted hydroxypropyl cellulose has an angle of repose of preferably 55° or less, more preferably 54° or less, still more preferably 53° or less from the standpoint of flowability of powder or reduced variation in weight of the tablet during the continuous tableting. The angle of repose of the low-substituted hydroxypropyl cellulose means an angle between a horizontal plane and a generatrix of the cone which has been formed by dropping powder continuously on the plane to be piled thereon. For example, it can be measured using a powder characteristics evaluation device "Powder Tester PT-S" (product of Hosokawa Micron Corporation).

The drug to be used for producing a solid preparation comprising the low-substituted hydroxypropyl cellulose in accordance with the invention is not particularly limited insofar as it is orally administrable. Examples of the drug include a central nervous system drug, a circulatory system drug, a respiratory system drug, a digestive system drug, an antibiotic, an antitussive and expectorant drug, an antihistamine drug, an antipyretic, analgesic and anti-inflammatory drug, a diuretic drug, an autonomic drug, an antimalarial drug, an anti-diarrheal drug, a psychotropic drug, and vitamins and derivatives thereof.

Examples of the central nervous system drug include diazepam, idebenone, paracetamol, naproxen, piroxicam, indomethacin, sulindac, lorazepam, nitrazepam, phenytoin, acetaminophen, ethenzamide, and chlordiazepoxide.

Examples of the circulatory system drug include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, and alprenolol hydrochloride.

Examples of the respiratory system drug include amlexanox, dextromethorphan, theophylline, pseudoephedrine, salbutamol, and guaifenesin.

Examples of the digestive system drug include a benzimidazole-based drug having an anti-ulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicyclic acid.

Examples of the antibiotic include talampicillin hydrochloride, bacampicillin hydrochloride, cefaclor, and erythromycin.

Examples of the antitussive and expectorant drug include noscapine hydrochloride, carbetapentane citrate, isoaminile citrate, and dimemorfan phosphate.

Examples of the antihistamine drug include chlorpheniramine maleate, diphenhydramine hydrochloride, and promethazine hydrochloride.

Examples of the antipyretic, analgesic and anti-inflammatory drug include ibuprofen, diclofenac sodium, flufenamic acid, sulpyrine, aspirin, and ketoprofen.

Examples of the diuretic drug include caffeine.

Examples of the autonomic drug include dihydrocodeine phosphate, dl-methylephedrine hydrochloride, atropine sulfate, acetylcholine chloride, and neostigmine.

Examples of the antimalarial drug include quinine hydrochloride.

Examples of the anti-diarrheal drug include loperamide hydrochloride.

Examples of the psychotropic drug include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate, and tranexamic acid.

In the production of the solid preparation containing the low-substituted hydroxypropyl cellulose, a disintegrant, a binder, an extender, a taste corrigent component, a flavor, a lubricant, and/or the like used commonly for a solid preparation may be used in a typical amount.

Examples of the disintegrant include corn starch, potato starch, partly pregelatinized starch, carboxymethyl starch sodium, carmellose, croscarmellose sodium, crystalline cellulose, and crospovidone.

Examples of the binder include hydroxypropyl cellulose, polyvinylpyrrolidone, and hydroxypropylmethyl cellulose.

Examples of the extender include erythritol, mannitol, sorbitol, lactose, sucrose, calcium phosphate, and calcium sulfate.

Examples of the taste corrigent component include citric acid, tartaric acid, and malic acid.

Examples of the flavor include menthol, peppermint oil, and vanillin.

Examples of the lubricant include magnesium stearate and sucrose fatty acid ester.

Next, a method for producing the low-substituted hydroxypropyl cellulose will be described.

Powdery pulp has a length-weighted mean width of from 10 to 25 µm, preferably from 15 to 24 µm, more preferably from 15 to 22 µm. When the powdery pulp has a length-weighted mean width of less than 10 µm, the low-substituted hydroxypropyl cellulose thus obtained has less swelling power and tablets obtained therefrom require longer disintegration time. When the powdery pulp has a length-weighted mean width of more than 25 µm, the low-substituted hydroxypropyl cellulose thus obtained has deteriorated flowability so that the variation in tablet weight becomes larger during tableting. The powdery pulp having a length-weighted mean width of less than 25 µm has not conventionally been used because it is believed that it has low fiber strength so that the fibers are easily cut into small pieces during compaction grinding and a reduction in the volume fractions of long and short fibrous particles deteriorates compressibility and causes capping.

The length-weighted mean length of the powdery pulp is preferably from 0.1 to 1.0 mm from the standpoint of adjustment efficiency or mixing properties with an alkali metal hydroxide solution.

The length-weighted mean width and length-weighted mean length of the pulp can be determined in accordance with the method (automated optical analysis) of JIS (Japanese Industrial Standards) P 8226. They can be measured using, for example, a Kajaani fiber length analyzer FS300 (product of Metso Automation Inc.).

As the pulp, wood pulp or cotton linter pulp may be used. The wood-derived pulp is particularly preferred from the standpoint of the absence of GMO (GMO: genetically modified organism). As the wood species, a needle-leaved tree such as pine, spruce or hemlock, or a broad-leaved tree such as eucalyptus or maple may be used.

The method for producing the low-substituted hydroxypropyl cellulose comprises the steps of: bringing powdery pulp having a length-weighted mean width of from 10 to 25 µm into contact with an alkali metal hydroxide solution to obtain alkali cellulose; reacting the alkali cellulose with propylene oxide to obtain a reaction product; neutralizing the alkali metal hydroxide present in the reaction product with an acid to precipitate crude low-substituted hydroxypropyl cellulose, in the absence of a step of dissolving a portion or all of the reaction product; washing the crude low-substituted hydroxypropyl cellulose to obtain washed low-substituted hydroxypropyl cellulose; drying the washed low-substituted hydroxypropyl cellulose to obtain a dried low-substituted hydroxypropyl cellulose; and pulverizing the dried low-substituted hydroxypropyl cellulose.

More specifically, first, starting material powdery pulp is brought into contact with an alkali metal hydroxide solution such as an aqueous sodium hydroxide solution to obtain alkali cellulose. The alkali cellulose may be obtained, for example, by adding dropwise or spraying the aqueous sodium hydroxide solution to the powdery pulp and mixing them in an internal stirring type reactor.

Next, the alkali cellulose is reacted with propylene oxide. The reaction may be carried out in the internal stirring type reactor following the production of the alkali cellulose, or the reaction may be carried out in another reactor into which the alkali cellulose produced has been introduced.

Then, the reaction product thus obtained is dispersed for neutralization in water or hot water comprising an acid such as acetic acid or hydrochloric acid in such an amount (equivalent amount) necessary for neutralizing the alkali metal hydroxide present in the reaction product to precipitate crude low-substituted hydroxypropyl cellulose. The equivalent amount required for neutralizing the alkali metal hydroxide present in the reaction product is an equivalent amount required for neutralizing the alkali metal hydroxide in the alkali metal hydroxide solution used for the contact with the pulp.

Next, the crude low-substituted hydroxypropyl cellulose is purified in the washing step, and then subjected to the drying step and the pulverization step to obtain desired low-substituted hydroxypropyl cellulose.

In the pulverization step, an impact pulverizer is preferably used. Examples of the impact pulverizer may include a hammer mill, an impact mill, and Victory mill. Further, it is preferred to sieve the pulverized low-substituted hydroxypropyl cellulose by a conventional method to remove coarse powder which has been insufficiently pulverized. A sieve having an opening of preferably from 75 to 200 μm may be used.

EXAMPLES

The invention will hereinafter be described specifically by Examples and Comparative Examples. It should not be construed that the invention is limited by or to Examples.
<Pulp Used>

Powdery Pulps A to D and sheet-like Pulp E were used. A length-weighted mean width and a length-weighted mean length of each of Pulps A to E was respective 23 μm and 0.5 mm for Pulp A, 21 μm and 0.5 mm for Pulp B, 17 μm and 0.4 mm for Pulp C, 13 μm and 0.4 mm for Pulp D, and 21 μm and 1.7 mm for Pulp E.

The length-weighted mean width and the length-weighted mean length of each of the powdery and sheet-like pulps were determined in accordance with the method of JIS P8226, by analyzing 50 mL of a dispersion prepared by sufficiently dispersing each pulp in water, with a Kajaani fiber length analyzer FS300 (product of Metso Automation Inc.).

Example 1

An internal stirring type reactor having an internal volume of 10 L was charged with 625 g of powdery Pulp A (600 g as an anhydrous portion) derived from wood and having a length-weighted mean width of 23 μm and a length-weighted mean length of 0.5 mm. The reactor was, while stirring, subjected to addition of 250 g of an aqueous sodium hydroxide solution having a concentration of 35% by weight. They were mixed at a jacket temperature of 45° C. for 30 minutes to obtain alkali cellulose containing 10% by weight of sodium hydroxide. Next, the reactor was purged with nitrogen and subjected to addition of 96 g (0.160 part by weight based on the anhydrous pulp) of propylene oxide. The resulting mixture was reacted at a jacket temperature of 60° C. for 2 hours while stirring to obtain 971 g of reaction product.

Next, the reactor was subjected to addition of 6562.5 g (100% of the neutralization equivalent) of 2% by weight acetic acid solution, and the resulting mixture was stirred for neutralization, thereby precipitating crude low-substituted hydroxypropyl cellulose. The precipitate was washed and dehydrated using a batch type centrifugal separator at a rotational speed of 3000 rpm, and then dried in a shelf dryer at 80° C. for 18 hours. The dried product was pulverized using an impact mill ("Victory Mill VP-1", product of Hosokawa Micron Corporation) and the pulverized product was sifted through a sieve having an opening of 150 μm to obtain low-substituted hydroxypropyl cellulose.

The hydroxypropoxy content of the low-substituted hydroxypropyl cellulose thus obtained was determined and as described below, the average particle diameter, volume fraction of various particles (long and short fibrous particles, spherical particles, and fine particles), compressibility and an angle of repose thereof were also determined. The results are shown in Table 1.
<Determination of Average Particle Diameter>

The average particle diameter was determined by measuring a diameter corresponding to the 50% cumulative value of a volume-based cumulative particle diameter distribution curve under conditions of a dispersion pressure of 2 bar and scattering intensity of from 2 to 10% by a dry method based on Fraunhofer diffraction theory by using a laser diffraction particle diameter distribution analyzer "Mastersizer 3000" (product of Malvern Instrument Ltd).
<Determination of Volume Fractions of Various Particles>

The volume fraction of each of various particles (long and short fibrous particles, spherical particles, and fine particles) was determined by a method comprising the steps of: subjecting sample particles to the measurement using a dynamic image analysis type particle diameter distribution analyzer "QICPIC/R16" (product of Sympatic GmbH) equipped with a constant feeder "VIBRI/L", an air-flow type disperser "RODOS/L", and an M7 lens under the conditions of a frame rate of 500 Hz, an injector of 4 mm, and a dispersion pressure of 1 bar to obtain images of the particles; analyzing the images of the particles by an analysis software "WINDOX5 Version:5.9.1.1" to find a number-based median EQPC, a number-based median LEFI, a number-based median DIFI, an elongation ratio, an aspect ratio, and a circularity of each of the particles; and calculating the volume fractions based on the values thus found, in accordance with the above-described equations. The division used during the analysis was M7.
<Determination of Compressibility>

The compressibility was determined by a method comprising the steps of: storing low-substituted hydroxypropyl cellulose in a desiccator (relative humidity: about 11%) of 25° C. containing a saturated aqueous solution of lithium chloride for one week to control the water content to from 2.8 to 3.8% by weight; compressing the stored low-substituted hydroxypropyl cellulose into a 450 mg tablet at a tableting pressure of kN (about 88.5 MPa) by using a table top type tablet press "HANDTAB 200" (product of ICHI-HASHI SEIKI) equipped with a round and flat punch having a diameter of 12 mm; and measuring the hardness of the tablet as the maximum strength at break when a load was applied to the tablet at a rate of 1 mm/sec in the tablet diameter direction by using a tablet hardness tester "TBH-125" (product of ERWEKA).
<Determination of Angle of Repose>

The angle of repose was determined by a method (injection method) of using a powder characteristics evaluation device "Powder Tester PT-S" (product of Hosokawa Micron Corporation), where sample powder was fed through a funnel onto a round table having a diameter of 80 mm until a constant angle was obtained, and the angle of the piled powder (an angle between the table and a mountain slope of the powder) was measured.

Example 2

Low-substituted hydroxypropyl cellulose was obtained in the same manner as in Example 1 except for the use of the powdery Pulp B derived from wood and having a length-weighted mean width of 21 µm and a length-weighted mean length of 0.5 mm. With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Example 3

Low-substituted hydroxypropyl cellulose was obtained in the same manner as in Example 2 except that the amount of propylene oxide was changed to 69 g (0.115 parts by weight based on the anhydrous pulp). With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Example 4

Low-substituted hydroxypropyl cellulose was obtained in the same manner as in Example 2 except that the amount of propylene oxide was changed to 126 g (0.210 parts by weight based on the anhydrous pulp). With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Example 5

Low-substituted hydroxypropyl cellulose was obtained in the same manner as in Example 1 except for the use of the powdery Pulp C derived from wood and having a length-weighted mean width of 17 µm and a length-weighted mean length of 0.4 mm. With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Example 6

Low-substituted hydroxypropyl cellulose was obtained in the same manner as in Example 1 except for the use of the powdery Pulp D derived from wood and having a length-weighted mean width of 13 µm and a length-weighted mean length of 0.4 mm. With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Comparative Example 1

Low-substituted hydroxypropyl cellulose was obtained in the same manner as in Example 2 except that the dried product was pulverized at 255 rpm for 60 minutes by using a batch type planetary ball mill "P-5" (product of Fritsch GmbH) and the pulverized product was sifted through a sieve having an opening of 106 µm. With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Comparative Example 2

A sheet-like Pulp E derived from wood and having a length-weighted mean width of 21 µm and a length-weighted mean length of 1.7 mm was immersed in an aqueous sodium hydroxide solution having a concentration of 43% by weight, and then pressed to obtain alkali cellulose containing 22.0% by weight of sodium hydroxide. A reactor was charged with 100 parts by weight of the resulting alkali cellulose and was purged with nitrogen. The reactor was then subjected to addition of 11.3 parts by weight of propylene oxide. The resulting mixture was reacted with stirring at a jacket temperature of 50° C. for 2 hours and then at a jacket temperature of 60° C. for 1 hour to obtain 108.0 parts by weight of reaction product. A kneader was charged with 250 parts by weight of warm water of 45° C. and 6.6 parts by weight (20% of the neutralization equivalent) of acetic acid. The reaction product was introduced and dispersed therein, and stirred at a jacket temperature of 45° C. for 40 minutes to dissolve a portion of low-substituted hydroxypropy cellulose. Then acetic acid (26.4 parts by weight, 80% of the neutralization equivalent) was added thereto for complete neutralization to crystallize crude low-substituted hydroxypropyl cellulose. The resulting crystallized product was dispersed in 3000 parts by weight of hot water of about 90° C. The dispersion was washed and dehydrated using a batch type centrifugal separator at a rotational speed of 3000 rpm, and then dried at 80° C. for 18 hours in a shelf dryer. The dried product was pulverized using an impact mill "Victory Mill VP-1" (product of Hosokawa Micron Corporation) and the pulverized product was sifted through a sieve having an opening of 75 µm to obtain low-substituted hydroxypropyl cellulose. With regards to the low-substituted hydroxypropyl cellulose thus obtained, the hydroxypropoxy content, average particle diameter, volume fractions of various particles (long and short fibrous particles, spherical particles, and fine particles), compressibility, and angle of repose were determined in the same manner as in Example 1. The results are shown in Table 1.

Tablets were produced using the low-substituted hydroxypropyl cellulose obtained above in each of Examples and Comparative Examples by the dry direct tableting method as described below, and a capping incidence was determined.

(1) Preparation of Drug Granules to be Tableted

Acetaminophen powder (490 g, product of Yamamoto Chemical Ind.) was placed in a fluidized-bed granulator "Multiplex MP-01" (product of Powrec Corp.). It was granulated, while spraying thereto 200 g of a 5% by weight aqueous solution of hydroxypropylmethyl cellulose (hydroxypropoxy content: 8.8% by weight, methyl content: 29.0% by weight, and viscosity at 20° C. of a 2% by weight aqueous solution thereof: 3.0 mPa·s, product of Shin-Etsu Chemical Co., Ltd.) under the conditions of an intake air temperature of 60° C., an air flow rate of from 0.5 to 0.7 m³/min, an exhaust air temperature of from 30 to 35° C., a spray air pressure of 200 kPa, and a spray rate of 10 g/min.

Then, after dried until the exhaust gas temperature reached 45° C., the dried granulated product was sifted through a sieve having an opening of 500 μm to obtain acetaminophen granules containing 98% by weight of acetaminophen.
(2) Tableting and Evaluation After 90 parts by weight of the acetaminophen granules were mixed with 10 parts by weight of low-substituted hydroxypropyl cellulose, 0.5 parts by weight of magnesium stearate as a lubricant was added thereto and mixed. The resulting mixture was tableted using a rotary tableting machine "VIRGO" (product of KIKUSUI SEISAKUSHO) at a tableting pressure of 12.5 kN (about 249 MPa) and a tableting rate of 20 rpm to obtain each tablet having a diameter of 8 mm, a curvature radius of 12 mm, and a tablet weight of 200 mg. The capping incidence of the tablets thus obtained was determined. The results are shown in Table 1.

Fifty tablets were put in the drum of a friability tester TA (product of ERWEKA GmbH) and rotated 100 times at 25 rpm for 4 minutes. Then the number of tablets having capping caused, that is, the number of tablets cracked into two layers was counted and a capping incidence was calculated based on the following equation:

Capping incidence (%)={(The number of tablets having capping)/50}×100 particles increased, while the more the volume fraction of long fibrous particles decreased. As a result, the product improved not only compressibility but also flowability with a reduced angle of repose. Although the compressibility of the low-substituted hydroxypropyl cellulose has been considered to be attributable to entanglement of fibrous particles, it becomes evident from the results of Examples 1, 2, 5, and 6 that among the fibrous particles, the long fibrous particles hardly contribute to the compressibility of the low-substituted hydroxypropyl cellulose but the short fibrous particles largely contribute thereto. This means that low-substituted hydroxypropyl cellulose having a greater volume fraction of the short fibrous particles has improved the compressibility. The short fibrous particles are considered to be contributive to compressibility due to easy re-arrangement by compression for formation of a dense product. On the other hand, the long fibrous particles are considered to be scarcely contributive to the compressibility due to a large primary particle size, making it difficult to form a dense product during compression.

Although low-substituted hydroxypropyl cellulose containing many fibrous particles has been considered to have deteriorated flowability, it is evident from the above results that the long fibrous particles are more contributive to

TABLE 1

| | length-weighted mean width of pulp (μm) | pulp shape | neutralization | pulverization | hydroxy-propoxy content (wt %) | average particle diameter (μm) | vol. fraction of long fibrous particles A (%) |
|---|---|---|---|---|---|---|---|
| Example1 | 23 | powder | entirely | impact mill | 11 | 68 | 29.4 |
| Example2 | 21 | powder | entirely | impact mill | 11 | 66 | 28.2 |
| Example3 | 21 | powder | entirely | impact mill | 8 | 68 | 28.9 |
| Example4 | 21 | powder | entirely | impact mill | 14 | 64 | 27.4 |
| Example5 | 17 | powder | entirely | impact mill | 11 | 63 | 24.9 |
| Example6 | 13 | powder | entirely | impact mill | 11 | 62 | 22.3 |
| Comp. Ex. 1 | 21 | powder | entirely | compaction grinding | 11 | 40 | 0.9 |
| Comp. Ex. 2 | 21 | sheet | partially | impact mill | 11 | 55 | 17.8 |

| | vol. fraction of short fibrous particles B (%) | vol. fraction of spherical particles (%) | vol. fraction of fine particles (%) | B/A | angle of repose (°) | compressibility (N) | capping incidence (%) |
|---|---|---|---|---|---|---|---|
| Example1 | 42.5 | 25.6 | 2.5 | 1.45 | 54 | 361 | 0 |
| Example2 | 43.9 | 26.1 | 1.8 | 1.56 | 53 | 370 | 0 |
| Example3 | 43.1 | 25.9 | 2.1 | 1.49 | 54 | 367 | 0 |
| Example4 | 44.5 | 26.4 | 1.7 | 1.62 | 53 | 378 | 0 |
| Example5 | 47.9 | 26.1 | 1.2 | 1.93 | 52 | 391 | 0 |
| Example6 | 51.2 | 25.8 | 2.3 | 2.30 | 51 | 415 | 0 |
| Comp. Ex. 1 | 18.6 | 69.2 | 11.2 | 20.7 | 42 | 154 | 18 |
| Comp. Ex. 2 | 13.0 | 63.4 | 5.8 | 0.73 | 43 | 109 | 10 |

The low-substituted hydroxypropyl cellulose being obtained in each of Examples 1, 2, 5 and 6, having a volume fraction of long fibrous particles of 20% or more and a volume fraction of short fibrous particles of 26% or more with the proviso that the volume fraction of short fibrous particles is greater than the volume fraction of long fibrous particles, and having a degree of hydroxypropoxy substitution of 11%, had high compressibility, was completely prevented from causing the capping, and had good flowability exhibiting an angle of repose of 55° or less. In addition, the more the length-weighted mean width of the powdery pulp decreased, the more the volume fraction of short fibrous deterioration in flowability than the short fibrous particles. Compared with short fibrous particles, long fibrous particles tend to entangle with each other so that an increase in long fibrous particles is considered to result in an increase in an angle of repose and deterioration in flowability.

The low-substituted hydroxypropyl cellulose obtained in each of Comparative Examples 1 and 2, having a volume fraction of long fibrous particles of less than 20%, a volume fraction of short fibrous particles of less than 26%, and a degree of hydroxypropoxy substitution of 11%, is powder having excellent flowability with a low angle of repose but having the capping caused due to low compressibility. In Comparative Example 1, it is considered that fibrous particles were cut into smaller pieces by compaction grinding, thereby reducing volume fractions of long and short fibrous particles. In Comparative Example 2 containing the step of dissolving a portion of the low-substituted hydroxypropyl cellulose, it is considered that a volume fraction of granular particles increased, while volume fractions of long and short fibrous particles decreased.

Further, it is evident from the results of Examples 3 and 4 that irrespective of the degree of hydroxypropoxy substitution, the low-substituted hydroxypropyl cellulose having a volume fraction of long fibrous particles of 20% or more and a volume fraction of short fibrous particles of 26% or more with the proviso that the volume fraction of short fibrous particles is greater than the volume fraction of long fibrous particles, has high compressibility, prevents the capping completely, and has good flowability with an angle of repose of 55° or less. Comparing the low-substituted hydroxypropyl cellulose obtained in each of Examples 2, 3 and 4 in which each pulp had the same length-weighted mean width, as the degree of hydroxypropoxy substitution increases, there is found to be a tendency that a volume fraction of long fibrous particles slightly decreases, while a volume fraction of short fibrous particles slightly increases. This is considered to occur because the increase in the degree of hydroxypropoxy substitution improves pulverization ability so that fibers are cut easily. However, the influence of the degree of hydroxypropoxy substitution on the volume fractions of the long and short fibrous particles is extremely restrictive compared with the influence of the length-weighted mean width of pulp on these volume fractions.

The invention claimed is:

1. Low-substituted hydroxypropyl cellulose having a hydroxypropoxy content of from 5 to 16% by weight, and having, on a basis of a dynamic image analysis to divide all particles into fine particles, spherical particles, and fibrous particles consisting of long and short fibrous particles, a volume fraction of the long fibrous particles relative to all of the particles of from 20 to 40% and a volume fraction of the short fibrous particles relative to all of the particles of from 26 to 60% with a proviso that the volume fraction of the short fibrous particles is greater than the volume fraction of the long fibrous particles,
wherein
the fine particles have a length of fiber of less than 40 μm,
the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimal Feret diameter to a maximal Feret diameter, of 0.5 or more, and a circularity, which is a ratio of a perimeter ($P_{EQPC}$) of a circle that has an area same as a projection area to a perimeter ($P_{real}$) of a real particle, of 0.7 or more,
the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7, and
the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

2. The low-substituted hydroxypropyl cellulose according to claim 1, having a ratio of the volume fraction of the short fibrous particles to the volume fraction of the long fibrous particles of from 1.35 to 2.50.

3. The low-substituted hydroxypropyl cellulose according to claim 2, having a volume-based average particle size, determined by a dry laser diffractometry, of from 10 to 120 μm.

4. A solid preparation comprising the low-substituted hydroxypropyl cellulose of claim 3.

5. The solid preparation according to claim 4, wherein the solid preparation is a tablet.

6. A solid preparation comprising the low-substituted hydroxypropyl cellulose of claim 2.

7. The solid preparation according to claim 6, wherein the solid preparation is a tablet.

8. The low-substituted hydroxypropyl cellulose according to claim 1, having a volume-based average particle size, determined by a dry laser diffractometry, of from 10 to 120 μm.

9. A solid preparation comprising the low-substituted hydroxypropyl cellulose of claim 8.

10. The solid preparation according to claim 9, wherein the solid preparation is a tablet.

11. A solid preparation comprising the low-substituted hydroxypropyl cellulose of claim 1.

12. The solid preparation according to claim 11, wherein the solid preparation is a tablet.

13. A method for producing the low-substituted hydroxypropyl cellulose according to claim 1, the method comprising:
bringing powdery pulp having a length-weighted mean width of from 10 to 25 μm into contact with an alkali metal hydroxide solution to obtain alkali cellulose;
reacting the alkali cellulose with propylene oxide to obtain a reaction product;
neutralizing the alkali metal hydroxide present in the reaction product with an acid to precipitate crude low-substituted hydroxypropyl cellulose, in the absence of a step of dissolving a portion or all of the reaction product;
washing the crude low-substituted hydroxypropyl cellulose to obtain washed low-substituted hydroxypropyl cellulose;
drying the washed low-substituted hydroxypropyl cellulose to obtain dried low-substituted hydroxypropyl cellulose; and
pulverizing the dried low-substituted hydroxypropyl cellulose.

* * * * *